United States Patent
Otagiri et al.

(10) Patent No.: US 7,166,577 B2
(45) Date of Patent: Jan. 23, 2007

(54) ALBUMIN HAVING ENHANCED ANTIMICROBIAL ACTIVITY

(75) Inventors: Masaki Otagiri, Kumamoto (JP); Takaaki Akaike, Kumamoto (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 10/976,708

(22) Filed: Oct. 29, 2004

(65) Prior Publication Data

US 2005/0222026 A1    Oct. 6, 2005

(30) Foreign Application Priority Data

Dec. 26, 2003    (JP) ............... 2003-433387

(51) Int. Cl.
*A61K 38/17*    (2006.01)
*C07K 14/765*    (2006.01)
*C12P 21/00*    (2006.01)

(52) U.S. Cl. .................. 514/12; 530/363; 435/69.6
(58) Field of Classification Search ............. 530/363; 574/2; 514/12; 435/69.6
See application file for complete search history.

(56) References Cited

FOREIGN PATENT DOCUMENTS

| | | |
|---|---|---|
| JP | 11-147838 A | 6/1999 |
| WO | WO 96/30006 A1 | 10/1996 |
| WO | WO 97/10265 A1 | 3/1997 |

OTHER PUBLICATIONS

Achilles Dugaiczyk, Simon W. Law, and Olivia E. Dennison (1982) Proc. Nat. Acad. Sci. U.S.A 79: 71-75.*
Jonathan S. Stamler*, Omar Jaraki*, John Osborne*, Daniel I. Simon*, John Keaney*, Joseph Vita*, David Singeli, C. Robert Valerlt, and Joseph LoScalzo (1992) Proc. Natd. Acad. Sci. USA 89: 7674-7677.*
Galliano M, Watkins S, Madison J, Putnam FW, Kragh-Hansen U, Cesati R, Minchiotti L. Eur J Biochem. (1998) 15; 329-34.*
Ewing JF, Young DV, Janero DR, Garvey DS, Grinnell TA (1997) J Pharmacol Exp Ther. 283(2):947-54.*
Richardson et al., "Potential therapeutic uses for S-nitrosothiols," Clinical Science 102:99-105, 2002.*
Ishima et al., J Pharm Soc Japan 123(Suppl. 4):161-164, 2003.*
Jia et al., *Nature*, 380: 221-226 (1996).
Miyamoto et al., *Biochimica et Biophysica Acta*, 1477: 90-97 (2000).
Stamler et al., *Proc. Natl. Acad. Sci. USA*, 89: 7674-7677 (1992).
Ishima et al., *J. Pharm. Soc. Jpn.*, 123, Suppl. 4: 161-164 (2003).

* cited by examiner

*Primary Examiner*—Jon Weber
*Assistant Examiner*—Rosanne Kosson
(74) *Attorney, Agent, or Firm*—Leydig, Voit & Mayer, Ltd.

(57) ABSTRACT

The present invention provides a nitrosylated albumin variant wherein one or more amino acid residues of constituent amino acid sequences are substituted, or a different amino acid residue is inserted into a part of the constituent amino acid sequences. The albumin variant has sufficient antimicrobial property and permits application as various useful pharmaceutical compositions.

11 Claims, 3 Drawing Sheets

Comparison of antimicrobial activities of various S-nitrosylated proteins in Salmonera. typhimuriumLT2

HPLC-flow reactor system

Buffer A
 0.1 M NaCl + 0.5 mM DTPA + 10 mM AcONa (pH 5.5)
Buffer B
 3 mM $HgCl_2$ + 10 mM AcONa (pH 5.5)
Buffer C
  Griess reagent Column A : gel filtration column
Column B : deproteinization column Residual rate of nitroso group of S-nitrosylated protein before and after freeze drying

ALBUMIN HAVING ENHANCED ANTIMICROBIAL ACTIVITY

FIELD OF THE INVENTION

The present invention relates to a nitrosylated albumin having an antimicrobial activity. More particularly, the present invention relates to an albumin having an enhanced antimicrobial activity, which is obtained by nitrosylating an albumin variant having a biological activity similar to that of natural albumin.

BACKGROUND OF THE INVENTION

Nitric oxide (NO) is a gaseous inorganic radical, which freely diffuses in plasma membrane in a living organism, and functions as an intracellular or intercellular signaling factor.

To the present, the biological action of NO has been widely studied from various aspects, and elucidated to cover a broad range of control of vascular function, function as a neurotransmitter, biological defense systems such as inflammatory response and immunological response and the like, and the like. On the other hand, for the disease state of infection or inflammation, NO becomes a major cause of cell and/or tissue damage via oxidation and nitration reaction of biological molecules of protein, nucleic acid and the like due to active nitric-oxide species derived from NO.

Recently, various NO donors have been developed and used as clinical pharmaceutical agents based on various such physiological activities of NO. In fact, S-nitroso glutathione (hereinafter GS-NO), which is a small nitrosothiol, is known to inhibit platelet aggregation but not decrease blood pressure, and applied as a platelet aggregation inhibitor for percutaneous transluminal coronary angioplasty (PTCA) and for the treatment of preeclampsia of pregnant women.

In addition, the active nitric-oxide species derived from NO is also known to have antimicrobial property, and, for example, GS-NO is known to have an antimicrobial activity. However, the antimicrobial activity of small nitrosothiols such as GS-NO is observed only at a high concentration of a few millimolars, and they are associated with insufficient aspects and many problems as a NO donor, such as short blood half life and an adverse influence exerted by a by-product generated simultaneously with NO release.

Incidentally, there are many reports on nitrosylated polymers as well, and, for example, Stamler. J. S. et al (WO96/30006, WO97/10265) have reported on the usefulness of nitrosylated proteins such as nitrosylated hemoglobin. However, inconsistent introduction rate of nitroso group into the protein can be easily anticipated because the proteins they used have plural cysteine residues. Moreover, the problems are feared that hemoglobin itself may act on vascular endothelial cells adversely, may lower renal function by deposition of iron component in the kidney tissue, and the like.

As other nitrosylated proteins, a nitrosylated form (hereinafter S—NO-α1-PI) of α1-protease inhibitor (hereinafter α1-PI) known as a major serine protease inhibitory protein in human serum has been reported (JP-A-11-147838, Y. Miyamoto, T. Akaike, H. Maeda, Biochimica Biophysica Acta, 1477, p. 90–97, (2000)). It has been reported that this S—NO-α1-PI shows an antimicrobial effect at a few micromolars and shows about 1000 times stronger antimicrobial activity as compared to that of GS-NO and the like.

Meanwhile, human serum albumin (HSA) is a major protein present in adult sera, which is produced by the liver and which functions as a carrier transporting various serum molecules. In addition, albumin plays an important role in maintaining the plasma oncotic pressure normally created by a solute (colloid) incapable of passing through capillary pores, thus maintaining the liquid content of blood. Thus, albumin is used for various treatments of conditions involving loss of liquid from blood vessels, such as surgical operation, shock, burn, hypoproteinemia causing edema and the like.

Stamler et al found nitrosylated albumin present in human plasma at the order of μM, and reported that hemoglobin cysteine residue in blood was nitrosylated. From these findings, nitrosylation of protein in living organisms is considered to be related to transportation and storage of NO and control physiological activity of NO (Stamler J. S. et al., Proc Natl Acad Sci USA, 89, p. 7674–7677, (1992), Lia J et al., Nature, 380, p. 221–226, (1996)).

Therefore, a nitrosylated form of albumin, which is present in the largest amount of the serum proteins and which plays a key role in living organisms is highly useful, and supply of stable nitrosylated albumin in clinical situations is significantly important. However, the reactivity of SH group of albumin is markedly lower than that of α1-PI and the like, and artificial and efficient nitrosylation of albumin has not been available.

SUMMARY OF THE INVENTION

There is a demand on the provision of albumin having sufficient antimicrobial property and permitting application as various useful pharmaceutical compositions, which is achieved by efficiently nitrosylating albumin.

In an attempt to solve the above-mentioned problems, the present inventors have analyzed efficiency of nitrosylation and antimicrobial activity thereof in various bacterial infection model animals, using an albumin variant having a mutation in one or more amino acid residues of constituent amino acid sequences, and, as a result, found that the albumin variant is efficiently nitrosylated, and its nitrosylated form shows a stronger antimicrobial activity than do NO and small nitrosothiols, and completed the present invention.

That is, the present invention relates to (1) a nitrosylated albumin variant wherein one or more amino acid residues of constituent amino acid sequences are substituted, or a different amino acid residue is inserted into a part of the constituent amino acid sequences, (2) the variant of the above-mentioned (1), wherein one or more amino acid residues of the constituent amino acid sequences are substituted by a sulfur-containing amino acid residue, (3) the variant of the above-mentioned (1), wherein an arginine residue of the constituent amino acid sequences is substituted by a sulfur-containing amino acid residue, (4) the variant of the above-mentioned (1), wherein an about 410th arginine residue of the constituent amino acid sequences is substituted by a cysteine residue, (5) the variant of the above-mentioned (1), wherein the number of the substituted or inserted amino acid residue is about 1 to 10, (6) the variant of the above-mentioned (1), wherein the albumin variant is a variant of human serum albumin, (7) the variant of the above-mentioned (1), wherein the albumin variant is produced by gene recombinantion technique, (8) the variant of the above-mentioned (1), wherein the albumin variant has a physiological activity similar to that of natural albumin,
(9) a nitrosylated albumin variant having an antimicrobial activity,
(10) a pharmaceutical agent comprising a variant of any of the above-mentioned (1) to (9), and
(11) a nitric oxide donor comprising a variant of any of the above-mentioned (1) to (9).

DETAILED DESCRIPTION OF THE INVENTION

Figure 1:
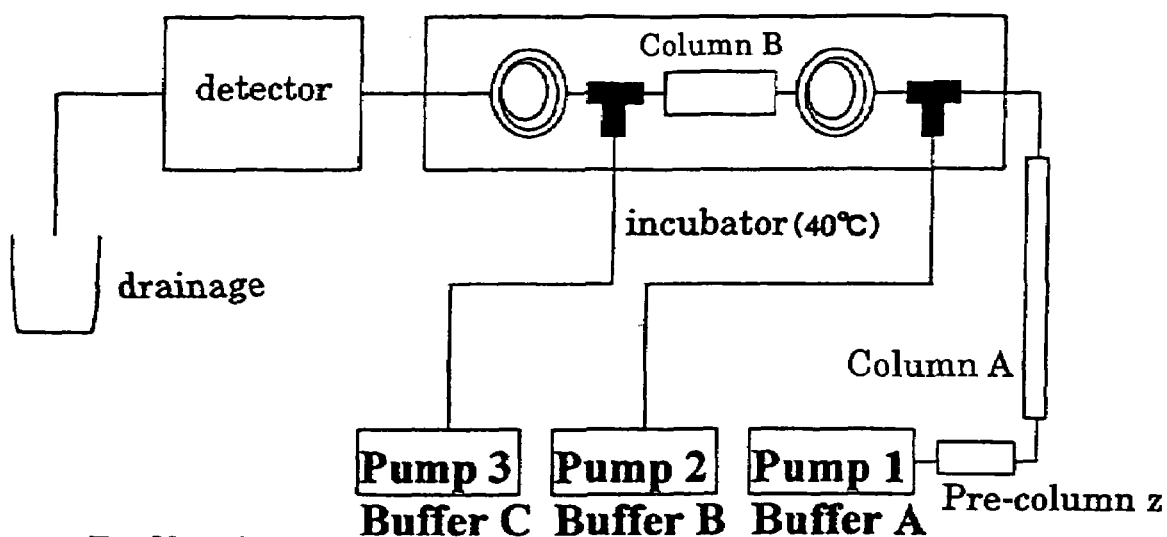
FIG. 1 explains a method of quantifying NO addition rate for an S-nitrosylated protein by HPLC.

The nitrosylated albumin variant of the present invention shows an antimicrobial activity at a lower concentration than do conventional antimicrobial agents. Therefore, an antimicrobial activity effective in living organism can be exhibited by only administering a pharmaceutical composition containing a small amount of a nitrosylated albumin variant.

The nitrosylated albumin variant of the present invention can be also used as one component of a pharmaceutical product as an NO (nitroso) donor.

Moreover, the nitrosylated albumin variant of the present invention can be preserved by freeze drying because the nitroso group can be stably present after freeze drying.

Moreover, the nitrosylated albumin variant of the present invention can be used safely without fear of infection with virus and the like by producing an albumin variant to be nitrosylated with gene recombinantion techniques.

In the present invention, nitrosylation means addition of a nitroso group (—NO). Nitrosylation of an albumin variant is preferably achieved by adding a nitroso group to a thiol group of the albumin variant and performed by a known method such as reaction with nitrite. While nitrosylation of proteins such as hemoglobin was successfully done in some cases, in general, nitrosylation of protein requires reactions under severe conditions. Thus, a method capable of introducing No into a thiol group under milder conditions is preferably employed, and a method using isoamylnitrite (De Master E. G. et al., Biochemistry, 34, p. 11494–11499, 1995) and a method comprising reaction with n-butylnitrite (Meyer D. J. et al., FEBS, Letters, 345, p. 177–180, 1994) can be preferably used.

In the albumin variant of the present invention, one or more amino acid residues of the constituent amino acid sequences are substituted or inserted. A preferable albumin variant is one wherein one or more amino acid residues of the constituent amino acid sequences are converted to sulfur-containing amino acid residues. As the sulfur-containing amino acid residue, cysteine residue, cystine residue and methionine residue can be mentioned, with particular preference given to cysteine residue. In addition, an albumin variant wherein an arginine residue of the constituent amino acid sequences is substituted by a sulfur-containing amino acid residue is preferable, and an albumin variant wherein about 410th arginine residue of the constituent amino acid sequences is substituted by a sulfur-containing amino acid residue is preferable. As the albumin variant of the present invention, an albumin variant wherein about 410th arginine residue of the constituent amino acid sequences is mutated to a cysteine residue (hereinafter HSA-R410C) can be preferably used.

In the albumin variant of the present invention, the number of the substituted or inserted amino acid residues is preferably about 1 to 10, more preferably about 1 to 5.

While the complete protein sequences of HSA have been already reported publicly (JP-A-8-228790 etc.), the protein sequences of HSA so far reported contain about 20 inconsistent residues, and the total number of amino acids of mature protein reported heretofore also varies. HSA-R410C, which is the above-mentioned albumin variant, is also naturally present in a small amount as one kind thereof. In the present invention, such an albumin naturally present in a small amount is also included in the albumin variants, as long as it is other than the albumin naturally present in the highest amount, which is referred to as natural albumin in the present invention. Moreover, the amino acid residue mutation site (Arg→Cys) of HSA-R410C used as one example in the present invention may be one or more positions different from the 410th position when the total number of amino acids differs.

The albumin variant of the present invention is preferably a variant of human serum albumin, and preferably a gene recombinant albumin. Serum albumin produced by fractionation of whole blood cannot be obtained in a large amount at a reasonable cost. However, when a gene recombination technique is adapted and a microorganism genetically engineered to efficiently produce albumin is used, the above-mentioned albumin variant and the like can be produced abundantly. The complete protein sequences of HSA have been already made public (JP-A-8-228790 etc.), and the albumin variant of the present invention can be produced by a method utilizing various known gene recombination techniques.

In addition, the albumin variant of the present invention preferably has the same physiological activity as does natural albumin. By the same physiological activity as does natural albumin is meant one having substantially the same function as natural albumin, such as not causing a rejection reaction in a living organism, maintaining normal osmolarity in blood flow, and function as a carrier to transport various serum molecules and the like.

An S-nitrosylated form of α1-PIox (hereinafter S—NO-α1-PIox), which is obtained by further S-nitrosylation of α1-PI (hereinafter α1-PIox) wherein methionine (Met), which is an active center of α1-PI, was chemically oxidized, was studied for its growth inhibitory activity on Salmonella typhimurium in vitro. As a result, it was reported that its antimicrobial activity was about 100 times stronger than that of S—NO-α1-PI and the S-nitrosylated form was capable of inhibiting growth of bacteria at a few dozen nanomolars (JP-A-11-147383, Y. Miyamoto, T. Akaike, H. Maeda, Biochimica Biophysica Acta, 1477, p. 90–97, (2000)). This suggests the possibility that, when S—NO-α1-PI produced at the site of infection is oxidized (oxidization of Met) by active oxygen species produced simultaneously with NO, the antimicrobial activity of an active form thereof may be further enhanced, and in the present invention, too, the antimicrobial activity is considered to be further enhanced by oxidization of methionine (Met) residue etc. of the albumin variant in the preliminary step toward nitrosylation.

A nitric oxide donor containing the albumin variant of the present invention can be used as an antimicrobial agent, a vascular circulatory failure improving agent, an antiplatelet agent, an ischemia/reperfusion injury suppressant and the like, which contain the variant as a major ingredient.

The present invention is explained in detail by referring to Examples and Reference Examples, which are not to be construed as limitative.

EXAMPLE 1

A recombinant protein of a human serum albumin variant (hereinafter HSA-R410C), wherein the 410th arginine (Arg) in the amino acid sequence of a human serum albumin (hereinafter HSA) has been mutated into cysteine (Cys), was prepared, 1,4-dithiothreitol (hereinafter DTT) was added in amount of 10 times the molar amount of the variant, and the mixture was reacted at 37° C. for 5 min to reduce SH group of free Cys residue in HSA. To confirm reduction of SH group of HSA by a DTT treatment, HSA and impurities such as DTT and the like were separated, after which SH group was quantified using the 5,5'-dithiobis-2-nitrobenzoic acid (DTNB) method, whereby the SH group of all free Cys residues was confirmed to have been reduced. Then, 0.1 M isoamyl nitrate was added in an amount 100 times the amount of DTT treated HSA. The mixture was reacted at 37° C. for 1 hr to allow nitrosylation to give nitrosylated HSA (S—NO-HSA).

COMPARATIVE EXAMPLE 1

A reaction similar to that in Example 1 was performed using a natural HSA (hereinafter nHSA) to give nitrosylated HSA (S—NO-nHSA).

COMPARATIVE EXAMPLE 2

A reaction similar to that in Example 1 was performed using an al-protease inhibitor (α1-PI) to give nitrosylated α1-PI (S—NO-α1-PI).

EXPERIMENTAL EXAMPLE 1

Quantification of NO Addition Rate of S-Nitrosylated Protein by HPLC

An NO addition rate of nitrosylated protein was quantified according to the method of Akaike et al (T. Akaike, et al., J. Biochemistry, 122, 459–466, 1997). To be specific, various S-nitrosylated proteins obtained in Example 1, Comparative Example 2 and Comparative Example 3, which were separated by HPLC shown in FIG. 1. Thereto was added $Hg^{2+}$ to give $NO^{2-}$ in the elution circuit, further mixed with a Griess reagent, and the flow reactor was constructed. An azo dye produced by the reaction of $NO^{2-}$ with the Griess reagent was measured at 540 nm, whereby various S-nitrosylated proteins were separated and quantified.

The results of measurement of NO addition rate of S—NO-protein by HPLC are shown in Table 1.

The NO introduction efficiency of Comparative Example 2 (S—NO-a1-PI) was about 1.0 (mol/molecule), whereas it was extremely low and about 0.3 (mol/molecule) in Comparative Example 1 (S—NO-nHSA).

In contrast, NO introduction efficiency of Example 1 (S—NO-HSA-R410C) was highly efficient and was about 1.30 (mol/molecule), whereby efficient nitrosylation was confirmed.

TABLE 1

NO addition rate of various S-nitrosylated proteins

| | number of SH group per molecule | NO addition rate (mol/molecule) |
|---|---|---|
| Example 1: HSA (R410) | 2 | 1.29 ± 0.09 |
| Comparative Example 1: nHSA | 1 | 0.29 ± 0.03 |
| Comparative Example 2: α₁PI | 1 | 1.00 ± 0.07 |

EXPERIMENTAL EXAMPLE 2

The nitroso group residual ratio of S-nitrosylated protein before and after freeze drying was measured.

Figure 2:
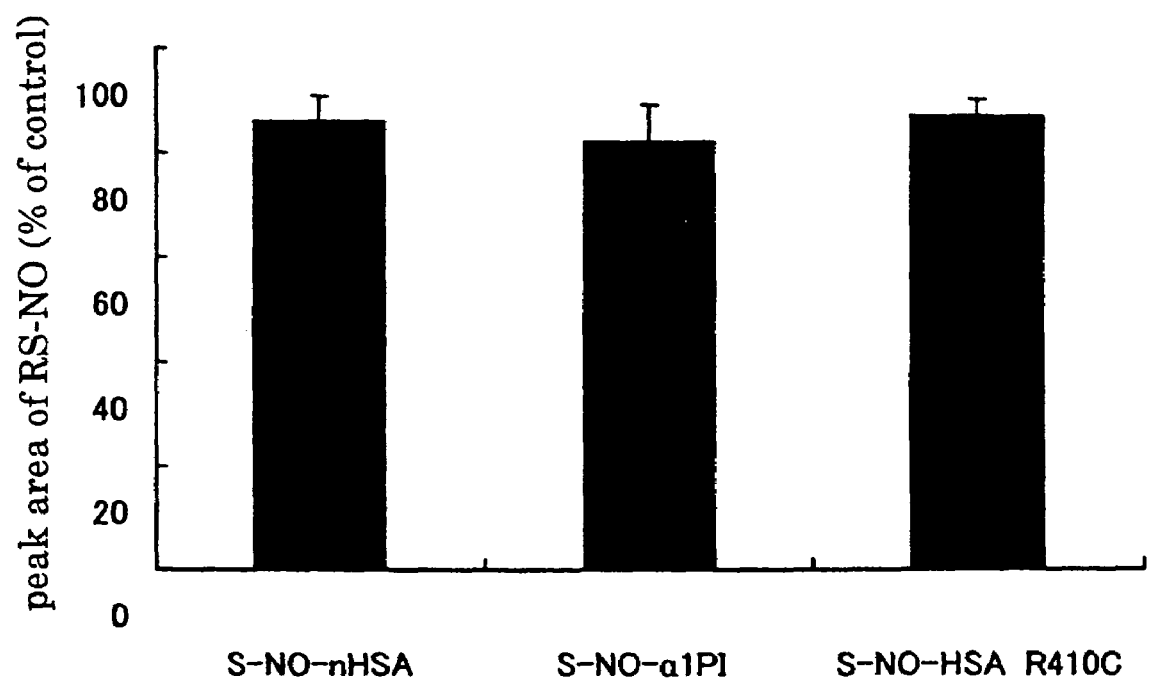
FIG. 2 shows a residual rate of a nitroso group of an S-nitrosylated protein before and after freeze drying.

Various S-nitrosylated proteins obtained in Example 1, Comparative Example 2 and Comparative Example 3 were dissolved in phosphate buffer (pH 7.4) containing 1 mM diethilenetriamine pentaacetic acid (DTPA), the residual amount of nitroso group was measured by HPLC, wherein its peak area was taken as 100% as a nitroso group residual amount at 0 hr, and the nitroso group was quantitatively determined to evaluate the residual amount. At the same time, the amount of the nitroso group before and after freeze drying was measured by HPLC, wherein the peak area before freeze drying was taken as 100%, and the residual amount of nitroso group was evaluated. The results are shown in FIG. 2.

As a result, various S-nitroso compounds obtained in Example 1, Comparative Example 1 and Comparative Example 2 all showed a high nitroso group residual ratio of not less than 80% after freeze drying relative to that before freeze drying.

While not shown in the data, the stability of S—NO-protein in the solution was examined and all S—NO-proteins were confirmed to be highly stable as evidenced by a half life of about 20 days.

EXPERIMENTAL EXAMPLE 3

Using *Salmonella typhimurium* LT2 strain, the activities of various S-nitroso compounds were compared.

The *Salmonella typhimurium* LT2 strain was cultured overnight in an M9 medium containing 20 wt % glucose ($Na_2HPO_4$ 64 g, $KH_2PO_4$ 15 g, NaCl 2.5 g, $NH_4Cl$ 5 g/1 L), washed 3 times with M9 and the number of bacteria was adjusted to $2 \times 10^6$ cfu/mL in an M9 medium. To this medium were added various S-nitrosylated proteins obtained in Example 1, Comparative Example 1 and Comparative Example 2, nitric oxide (NO) or S-nitroso glutathione (GS-NO) as Comparative Example, and the mixture was reacted at 37° C. for 9 hr, after which the absorbance at wavelength 655 nm was measured and the ratio based on the absorbance of the control group without addition as 100% was calculated as a growth rate (%).

Figure 3:
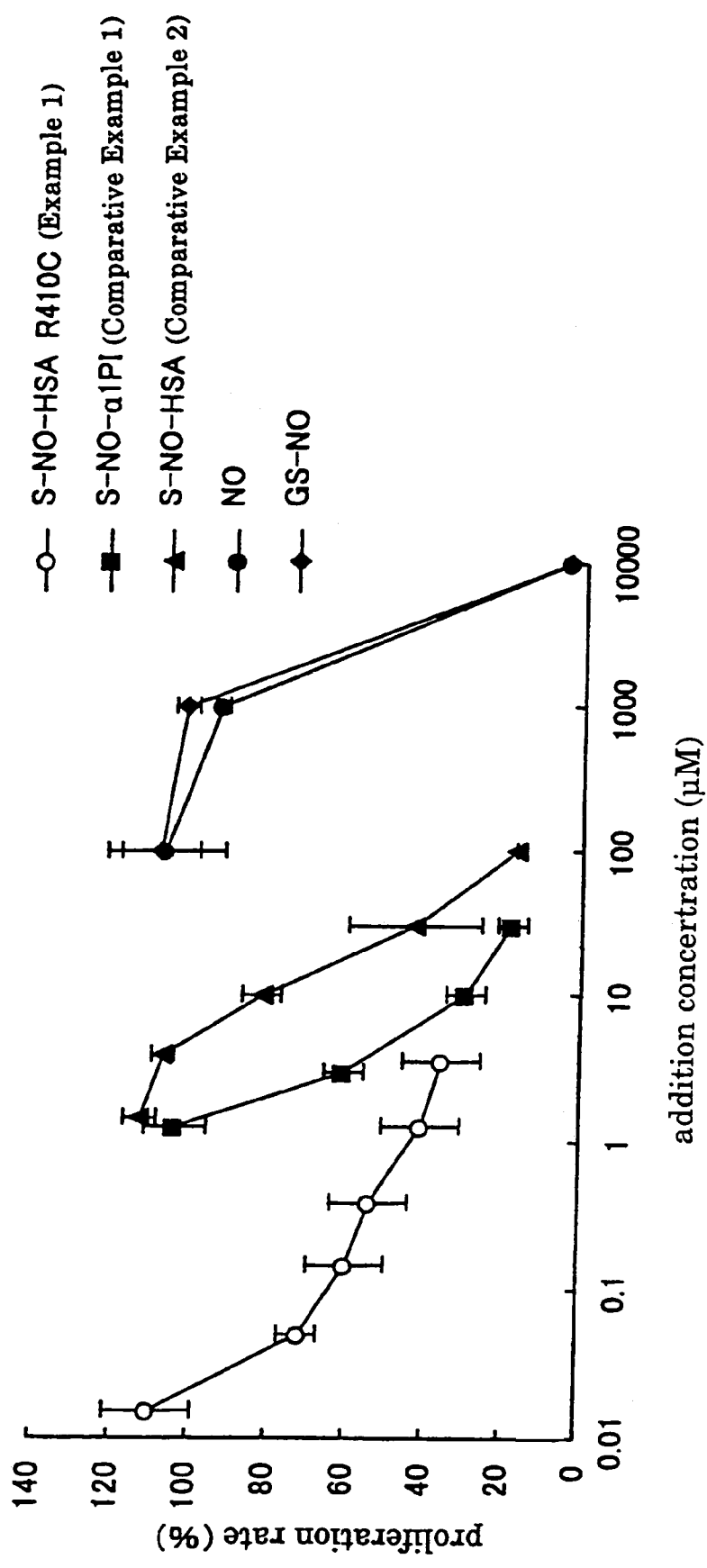
FIG. 3 shows antimicrobial activity of various S-nitrosylated proteins.

The results are shown in FIG. 3. In Example 1, a strong antimicrobial activity was observed as compared to NO and small GS-NO, and also a superior antimicrobial activity was observed as compared to Comparative Example 1 and Comparative Example 2.

Therefore, the S-nitrosylated serum protein of the present invention has been shown to have a stronger antimicrobial activity as compared to NO, small GS-NO and the like.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the appended claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. All methods described herein can be performed in any suitable order unless otherwise indicated herein or otherwise clearly contradicted by context. The use of any and all examples, or exemplary language (e. g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

This application is based on application No. 2003-433387 filed in Japan, the contents of which are incorporated hereinto by reference.

What is claimed is:

1. An isolated or purified nitrosylated albumin variant of an amino acid sequence of human serum albumin, wherein the 410$^{th}$ arginine residue of the amino acid sequence of human serum albumin set forth in SEQ ID NO: 1 is substituted by a cysteine residue and wherein an average number of nitric oxide (NO) molecules per molecule of the nitrosylated albumin variant is more than about 0.3.

2. The variant of claim 1, wherein the albumin variant is produced by gene recombination technique.

3. The variant of claim 1, wherein the albumin variant has at least one of the following physiological activities (a) to (c)

similar to those of natural albumin: (a) not causing a rejection reaction in a living organism, (b) maintaining normal osmolarity in blood, and (c) functioning as a carrier to transport serum molecules.

4. The variant of claim 1, wherein the albumin variant has an antimicrobial activity.

5. The variant of claim 1, wherein the average number of NO molecules per molecule of the nitrosylated albumin variant is more than about 1.3.

6. A method of producing a nitrosylated albumin variant of an amino acid sequence of human serum albumin, which method comprises contacting a human serum albumin variant with a nitrosylating agent to obtain a nitrosylated albumin variant of an amino acid sequence of human serum albumin, wherein the $410^{th}$ arginine residue of the amino acid sequence of human serum albumin set forth in SEQ ID NO: 1 is substituted by a cysteine residue and wherein an average number of nitric oxide (NO) molecules per molecule of the nitrosylated albumin variant is more than about 0.3.

7. A method of treating bacterial infection, platelet aggregation, vascular circulatory failure, or ischemia/reperfusion injury, which method comprises administering an effective amount of a nitrosylated albumin variant of an amino acid sequence of human serum albumin to a subject wherein the $41^{th}$ arginine residue of the amino acid sequence of human serum albumin set forth in SEQ ID NO: 1 is substituted by a cysteine residue and wherein an average number of nitric oxide (NO) molecules added per molecule of the nitrosylated albumin variant is more than about 0.3.

8. The variant of claim 1, wherein the average number of NO molecules per molecule of the nitrosylated albumin variant is about 1.3.

9. The variant of claim 1, wherein the average number of NO molecules per molecule of the nitrosylated albumin variant is not more than about 1.3.

10. A composition comprising the variant of claim 1.

11. The composition of claim 10, wherein the composition is a pharmaceutical composition further comprising a pharmaceutically acceptable carrier.

\* \* \* \* \*

UNITED STATES PATENT AND TRADEMARK OFFICE
CERTIFICATE OF CORRECTION

PATENT NO. : 7,166,577 B2 Page 1 of 1
APPLICATION NO. : 10/976708
DATED : January 23, 2007
INVENTOR(S) : Otagiri et al.

It is certified that error appears in the above-identified patent and that said Letters Patent is hereby corrected as shown below:

Claim 1, at column 9, line 65, "the 410$^{th}$ arginine residue" should read "the arginine residue at position 410"

Claim 6, at column 11, line 15, "the 410$^{th}$ arginine residue" should read "the arginine residue at position 410"

Claim 7, at column 12, line 4, "41$^{th}$ arginine residue" should read "the arginine residue at position 410"

Claim 7, at column 12, line 7, "(NO) molecules added per molecule" should read "(NO) molecules per molecule"

Signed and Sealed this

Third Day of July, 2007

JON W. DUDAS
*Director of the United States Patent and Trademark Office*

SEQUENCE LISTING

```
<160> NUMBER OF SEQ ID NOS: 1

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220
```

-continued

```
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Lys Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585
```